PLANTS
SUBCLASS
55
June 5, 1951 A. VECA Plant Pat. 1,014
AZALEA PLANT
Filed Dec. 29, 1949
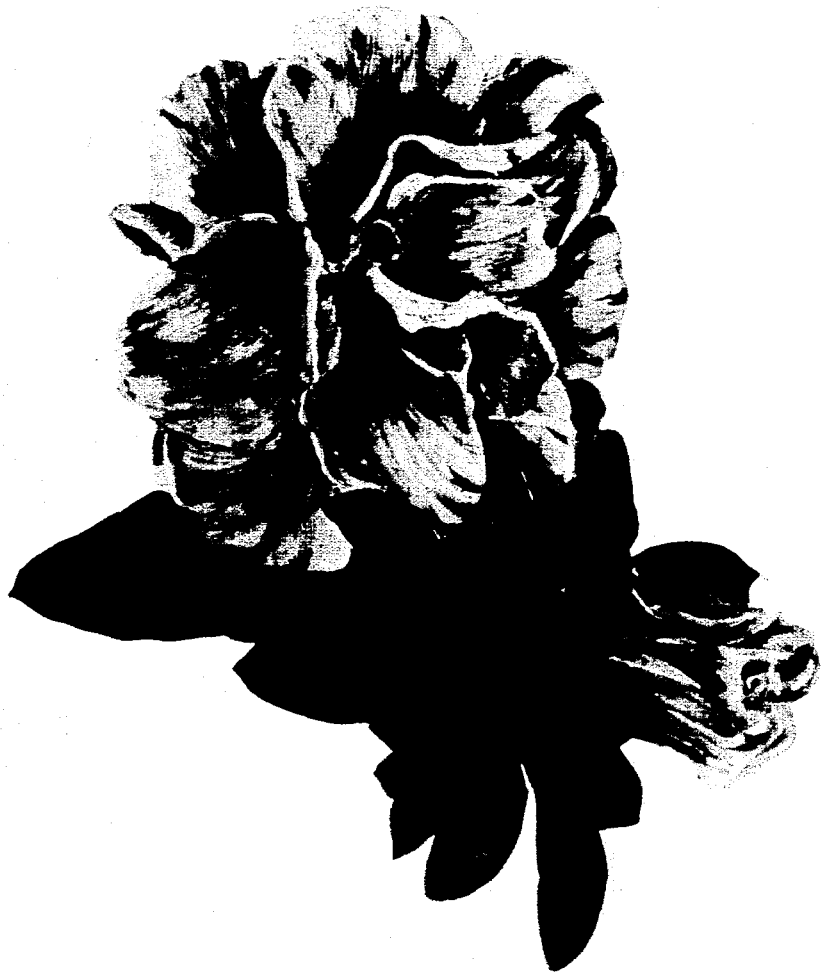
ANTONINO VECA
INVENTOR.
BY Albert J. Fike
ATTORNEY

SEARCH ROOM

Patented June 5, 1951

Plant Pat. 1,014

UNITED STATES PATENT OFFICE 1,014

AZALEA PLANT

Antonino Veca, Pico, Calif.

Application December 29, 1949, Serial No. 135,751

1 Claim. (Cl. 47—60)

This invention relates to a distinct improvement in azalea plants and the present development is of the Belgium Indica variety.

The new azalea is related to the rhododendron family and originated as a sport and is not the result of hybridization or cross-breeding. The sport was of an azalea triumph natural mutation parentage and the plant was reproduced at Pico, California, asexually from cuttings and graftings.

The accompanying illustration, which is a part of this specification, shows a plant of this variety of azalea in approximately its true colors.

*The plant*

The plant is medium fast growing and will produce flowering plants the first year. A distinctive feature of this azalea is the truss formation or flowering branches. This formation is similar to the Belgian Indica azaleas, except that each branch every year sends out from its terminal bud two to four branchlets. These branchlets are short and after a few seasons' growth, the plant has a very compact and dense appearance over its surface area.

*The foliage*

The foliage is evergreen and new growth is a good medium green turning darker with maturity. The leaves are medium to small, being approximately one and one-half inches long and one-half inch wide. When the old leaves fall off, they are immediately replaced by new ones.

*The flowers*

The flowers are large, measuring a good three inches in diameter, and this particular variety has two rows of petals. The petals are so arranged that the blossoms appear to be nearly fully double, as shown in the drawings. The petals are so divided and arranged that they appear as thirteen to fifteen in number. Both petals are joined in the corolla at nearly the same joint and the edges of the petals are somewhat curled, thus giving more of a double appearance to the blossom. One half of each petal is deeply flecked with red, thus giving the blossom a deep red colored throat, as will be obvious from the drawings. The colors of the petals range from a Pansy Purple, as shown in the dictionary of color published by Maerz and Paul at Plate 54–L–8, to Sweet Briar, shown at Plate 1–C–4 in the same publication.

*The stamens*

The stamens are usually in threes, short with small anthers and somewhat indistinct. The style protrudes beyond the petals.

This new azalea has a more compact habit of growth and a new color combination distinguishing it from others, particularly the pink blush on a white background with a deep red throat. The blooming season is January through April and the plant is well adapted for potting and forcing, particularly because of its compact growth. The plant by flowering the first year is much faster than other azaleas and this particularly variety can be forced for Christmas blooming, as well as late spring blooming.

For best results, this variety should be grafted on *Rhododendron coccinea* root stock. This procedure will give a much more compact habit of growth and produce a more flowering type of plant than would be possible than by any other method. This variety has proven to be resistant to leaf spot and no damage from thrip has ever been encountered. It is one of the best azaleas for growing in the full Southern California sun while, at the same time, it will withstand temperatures well below freezing without damage.

When the plant blooms, it appears to be a solid mass of blossoms. Another feature is the unusual green tinge on the outer edge of the bud from the time that it first starts to bloom right up to the full blooming period.

Having thus disclosed my invention, I claim:

The new and distinct variety of azalea plant herein described and illustrated, characterized particularly by its rapid growth, early and full blooming the first year, its compactness, the large double many petaled flowers in colors ranging from pink at the edge to a deep red at the throat on a white background and a green tinge on the outer edge of the bud from the time it starts to bloom up to its full blooming period.

ANTONINO VECA.

REFERENCES CITED

The following references are of record in the file of this patent:

UNITED STATES PATENTS

| Number | Name | Date |
|---|---|---|
| Pl. Pat. 675 | Leach | Apr. 9, 1946 |
| Pl. Pat. 733 | Dauernheim | Apr. 1, 1947 |